(12) United States Patent
Zhang (10) Patent No.: US 7,979,103 B2
(45) Date of Patent: Jul. 12, 2011

(54) CATHETER-FREE IMPLANTABLE NEEDLE BIOSENSOR

(75) Inventor: Yanan Zhang, Northridge, CA (US)

(73) Assignee: San Meditech (Huzhou) Co., Ltd., Huzhou (CN)

( * ) Notice: Subject to any disclaimer, the term of this patent is extended or adjusted under 35 U.S.C. 154(b) by 684 days.

(21) Appl. No.: 11/262,373

(22) Filed: Oct. 29, 2005

(65) Prior Publication Data

US 2008/0033269 A1  Feb. 7, 2008

(30) Foreign Application Priority Data

Dec. 8, 2004 (CN) .......................... 2004 1 0101080

(51) Int. Cl.
*A61B 5/05* (2006.01)

(52) U.S. Cl. ........................................ 600/345; 600/377

(58) Field of Classification Search .......... 600/345–348, 600/354, 360, 365–366, 372, 373, 377, 382, 600/384, 393–397; 204/403.01–415
See application file for complete search history.

(56) References Cited

U.S. PATENT DOCUMENTS

| | | | | |
|---|---|---|---|---|
| 4,685,466 A | * | 8/1987 | Rau | 600/387 |
| 4,919,141 A | * | 4/1990 | Zier et al. | 600/345 |
| 4,953,552 A | * | 9/1990 | DeMarzo | 600/347 |
| 5,063,081 A | * | 11/1991 | Cozzette et al. | 435/4 |
| 5,094,242 A | * | 3/1992 | Gleason et al. | 600/377 |
| 5,211,175 A | * | 5/1993 | Gleason et al. | 600/548 |
| 5,800,420 A | * | 9/1998 | Gross et al. | 604/890.1 |
| 5,848,990 A | * | 12/1998 | Cirelli et al. | 604/136 |
| 6,219,574 B1 | * | 4/2001 | Cormier et al. | 604/20 |
| 6,256,533 B1 | * | 7/2001 | Yuzhakov et al. | 604/21 |
| 6,379,324 B1 | * | 4/2002 | Gartstein et al. | 604/22 |
| 6,549,797 B1 | * | 4/2003 | Leonard et al. | 600/372 |
| 6,591,133 B1 | * | 7/2003 | Joshi | 604/21 |
| 6,952,604 B2 | * | 10/2005 | DeNuzzio et al. | 600/345 |
| 7,120,483 B2 | * | 10/2006 | Russell et al. | 600/345 |
| 7,228,162 B2 | * | 6/2007 | Ward et al. | 600/345 |
| 7,429,258 B2 | * | 9/2008 | Angel et al. | 604/173 |
| 7,651,475 B2 | * | 1/2010 | Angel et al. | 604/65 |
| 2005/0004438 A1 | * | 1/2005 | Ward et al. | 600/345 |
| 2006/0258959 A1 | * | 11/2006 | Sode | 600/584 |

* cited by examiner

*Primary Examiner* — Charles A Marmor, II
*Assistant Examiner* — Navin Natnithithadha
(74) *Attorney, Agent, or Firm* — Jen-Feng Lee, Esq.

(57) ABSTRACT

Electrochemical biosensors consisting of two or more needle-shaped electrodes for monitoring of molecules such as glucose in the subcutaneous tissue are provided. The two electrodes are parallel to each other, and are fixed perpendicularly to the planar side of a sensor base which provides skin fixation and electric connection. The needle electrodes are made of rigid conducting materials, capable of inserting into the skin without the need of catheters. One electrode is the sensing electrode and the other, the reference electrode. A compound sensing membrane is attached onto the sensing electrode surface to detect analyzed molecules.

1 Claim, 7 Drawing Sheets

CATHETER-FREE IMPLANTABLE NEEDLE BIOSENSOR

CROSS-REFERENCE TO RELATED APPLICATIONS

The present application claims the benefit of prior filed Chinese Patent Application entitled "Implantable Needle Bio-sensor" with application date Dec. 8, 2004, and application number 2004101010806.

BACKGROUND OF THE INVENTION

1. Field of the Invention

The present invention relates to electrochemical implantable sensor assemblies for monitoring molecules such as Glucose and Oxygen in subcutaneous tissue.

2. Description of the Prior Art

Apparatus utilizing biosensors as measurement components can directly measure biochemical properties of molecules without complex separation steps or additional reagents. Apparatus with electrochemical sensors obtain such properties by measuring electrical signals generated from electrochemical redox reactions of the molecules.

Implantable sensors have the advantage of directly monitoring molecule properties of medical importance, such as concentration of oxygen, glucose and lactate. Such information can be used to improve the accuracy of diagnosis, or the effectiveness of treatment. A subcutaneous micro-sensor directly placed in the physiological cellular environment where metabolism takes place can provide more accurate and timely information of the physiological state. For example, the change of glucose concentration for a diabetic patient is often unpredictable due to a number of factors such as diet, temperature, emotional states, physical activities, age, and rate of metabolism, etc. While discrete measurements cannot provide enough information of dynamic changes, continuous monitoring can in essence provide information that can dramatically improve diagnoses and treatment of diseases.

Reactions of the tissue to an implanted device typically include two types: the first is the tissue's reaction to a foreign body at the cellular and molecular level, which is the mechanism of physiological reactions against a foreign object; the second is the wound healing reaction process that involves a series of time related tissue regeneration steps. Both processes cause perturbation at the implant-tissue interface, forming barrier layer (scar tissue, for example). Such phenomenon may not be a serious problem for some implants of mechanical function (such as artificial bones, ligament, valves, etc.). But for a sensor intended to measure molecules at the interface, the barrier layer isolates the sensor from the ambient issue environment, thus prevents or impairs the molecule infiltration between the sensor and the tissue fluid. Therefore, the sensor measurement would not reflect true molecule properties of the tissue.

The degree of interaction between implanted sensor and the tissue is usually described by "biocompatibility". One aspect of biocompatibility is biochemical. It may involve physiological reactions such as immune, inflammatory, and anaphylactic reactions caused by the chemical ingredients, additives, or degradation products of the implant. Another aspect of the biocompatibility is mechanical: the physical characteristics of the implanted object such as surface roughness, shape, size, etc. that could cause various degrees of irritations and damages to the tissue. Furthermore, most of the known implanted sensors require auxiliary devices such as catheters or cannula for implanting. Some even requires an incision or surgery. The extra damage to the tissue by the assisting devices is often major factors affecting the performance of the sensors.

Another important factor is the disturbance to the normal physiological environment caused by an excessive flux of molecules consumed by or released from the sensor measuring process. Since the molecules to be detected participate in physiological processes, the more the reaction consumes/releases, the more serious is the interference to the tissue. A lower rate of molecular consumption per unit area (flux) can always be expected to produce a lower degree of disturbance to the tissue. Most sensor designs feature a very small active sensing area while majority of the implanted parts only serves as the supporting body. Such devices require high flux in a very small area to obtain favorable signal. Thus, the localized high molecular flux can result in strong disturbance to the tissue environment and can cause sensor inaccuracy and instability.

Finally, when there are no conventional equipments readily available, problems often exist when attempt is made to mass-produce complicated micro-biosensors involving biochemical processes. Therefore, a simple design with reliable manufacturability is a key for product quality and reliability.

SUMMARY OF THE INVENTION

The present invention overcomes the disadvantage of using catheter to implant sensors. The present invention provides subcutaneously implanted needle shaped sensors, with minimal diameter and large sensing surface area. The sensor electrodes can be directly inserted into the skin, without the need of a catheter. It is essentially painless for the procedure of implanting and the entire duration of use.

In a preferred embodiment, the sensor assembly of the present invention comprises a base with a planar bottom side, and elongated thin needle electrodes fixed perpendicularly to the base. Connection circuits are connected to the electrodes on the topside of the base.

The sensor assembly has at least one cathode and one anode. The number of electrodes may be two, three or four, one of which may be cathode and the rest anodes; or, one of the electrodes may be anode and the rest cathodes.

In a preferred embodiment, the anode comprises a hard metal needle core, covered by (in turn) a noble metal layer, a platinum layer, and a biosensing layer. The cathode comprises a hard metal needle core, covered by (in turn) a silver layer, a silver chloride layer, and a polymer diffusion layer. Such a configuration is intended for hydrogen peroxide detection based sensors.

The bio-sensing layer is a complex membrane wherein the inner layer contains enzyme and the outer layer contains biocompatible polymers and possesses molecular diffusion limiting characteristics.

In another embodiment of the invention, the anode may have a metal needle core, covered by (in turn) a silver layer and a polymer layer. The cathode may have a metal needle core, a covered by (in turn) a platinum layer, and a bio-sensing layer. Such configuration is for oxygen detection based sensors.

There may be a medical adhesive tape affixed to the bottom of the base for attaching the sensor assembly to the skin.

On the upper surface of the base, there may be electric receptacles (or circuit connections) for connecting the electrodes to an amperometric instrument.

The diameter of the needle electrode core in this invention may be in the range of 0.1-0.3 mm.

In the present invention of the miniature sensor assembly, the two needle electrodes are perpendicularly fixed to the bottom of the base, and are connected to a portable amperometric device through a receptacle on the top of the base. The implanted portion can be directly inserted into the skin without the need of a catheter. The damage to the tissue by such a implanting procedure is minimal. Moreover, because the electrode surface is utilized to near 100 percent, the material exchange rate (molecules in and out of the contact interface of sensor membrane and tissue) around the electrode can be adjusted to minimum while still achieving high overall sensitivity. Such a mechanism can effectively reduce the disturbance to the tissue and ensure that the sensor can truly detect normal state of tissue physiology. In the present invention, the needle electrodes have very small diameters (0.1-0.3 mm), miniature needles of this size cause essentially no pain. In terms of manufacturability, since the needle electrodes are separately fabricated and assembled, complicated manufacturing processes can be easily separated into simple steps, making it easier for mass production and quality control.

DETAILED DESCRIPTION OF THE PRESENT INVENTION

The present invention provides subcutaneously implanted sensor assembly with two or more separate parallel needle shaped electrodes, wherein the electrodes have diameters approximately 0.2 mm and large sensing surface areas. The electrodes can be directly inserted into the skin, without the need of a catheter. The damage to the surrounding tissue due to the insertion of the sensor is minimum. It is normally painless for the procedure of implanting and the entire duration of use. The needle electrodes are affixed perpendicular to the sensor base bottom surface, and easy to operate for implantation. The physiological tissue fluid surrounding the electrodes serves as the conductive electrolytes, within the normal physiological pH value.

One advantage of the present invention is that about 100% of the implanted sensor surface is working electrode surface, which maximizes the contact surfaces between electrode and tissue fluid. This will reduce molecule exchange flux between the electrode and tissue while obtaining high degree of sensitivity. Therefore, the overall accuracy and signal stability of the measurement is significantly improved.

Another advantage of the present invention is that the vertical subcutaneous implantation is basically painless, comparing with conventional implanted devices which may cause various degree of pain. The present invention features the smallest diameters of all current known subcutaneously implanted sensors.

The present invention reduces the effective diameter of the electrode approximately 0.2 mm. This becomes possible by separating complicated structure and production processes based on the principal of separate cathode and anode. The manufacturing process is simple, easy to repeat and easy for quality control.

The electrochemical sensor assembly of the present invent comprises at least one cathode and one anode. The number of the electrodes may be two, three or four, one of which may be cathode and the rest anodes; or, one of the electrodes may be anode and the rest cathodes.

The needle electrodes may have rigid metal cores that are of corrosion resistant conductive materials such as stainless steel, barium alloy, and titanium alloy.

The sensor assembly may have one cathode and one anode. In case of two-electrode system, the sensor assembly is for short-term use. When used for hydrogen peroxide in electrochemical oxidation measurement, the anode is an indicating electrode, with stainless steel, beryllium bronze, titanium alloy as base material, and platinum deposition as surface material; the cathode is a reference/counter electrode, with stainless steel, beryllium bronze, titanium alloy as base material, and silver or silver chloride as surface material. When used for oxygen detection in electrochemical reduction measurement, the anode is made of stainless steel, beryllium bronze, titanium alloy as base material, and silver as surface material; the cathode is made of stainless steel, beryllium bronze, titanium alloy as base material, and platinum as surface material. Counter electrode material (silver/silver chloride) may be consumed during use. The system, therefore, has a limited lifetime.

Long-term use sensor assembly should be three-electrode system: platinum or other non-active metal is the surface material for the third needle electrode which is the assisting electrode for carrying electric current, wherein the reference electrode only provides reference voltage, does not carry electric current. The system will not consume reference electrode materials, and can be used for long term application.

The needle shaped electrodes and their outer sensing layer should possess integrated strength, should be able to withstand the friction and contact with skin and tissue during implantation and measurement. This requires that the sensing membrane have firm attachment to the electrode metal and have enough physical strength.

Figure 2:
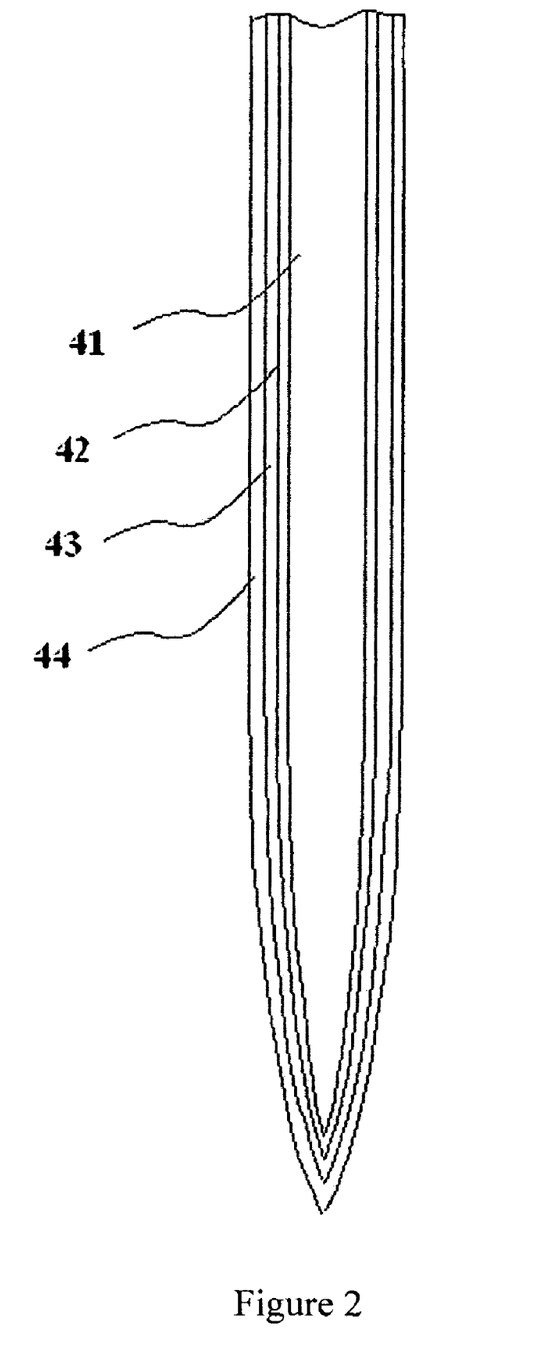
FIG. 2 is a cross section view of a needle anode structure in accordance with the invention.

As seen in FIG. 2, the anode comprises an anode needle core 41, a first anode cover layer 42, a second anode cover layer 43, and a third anode cover layer 44, wherein the anode needle core 41 is a needle shaped metal core in the center of the anode, covered by the first anode cover layer 42, which in turn is covered by the second anode cover layer 43, which in turn is covered by the third anode cover layer 44. In a preferred embodiment, the anode needle core 41 is a hard metal needle core; the first anode cover layer 42 is a noble metal layer; the second anode cover layer 43 is a platinum layer; and the third anode cover layer 43 is a bio-sensing layer.

Figure 2A:
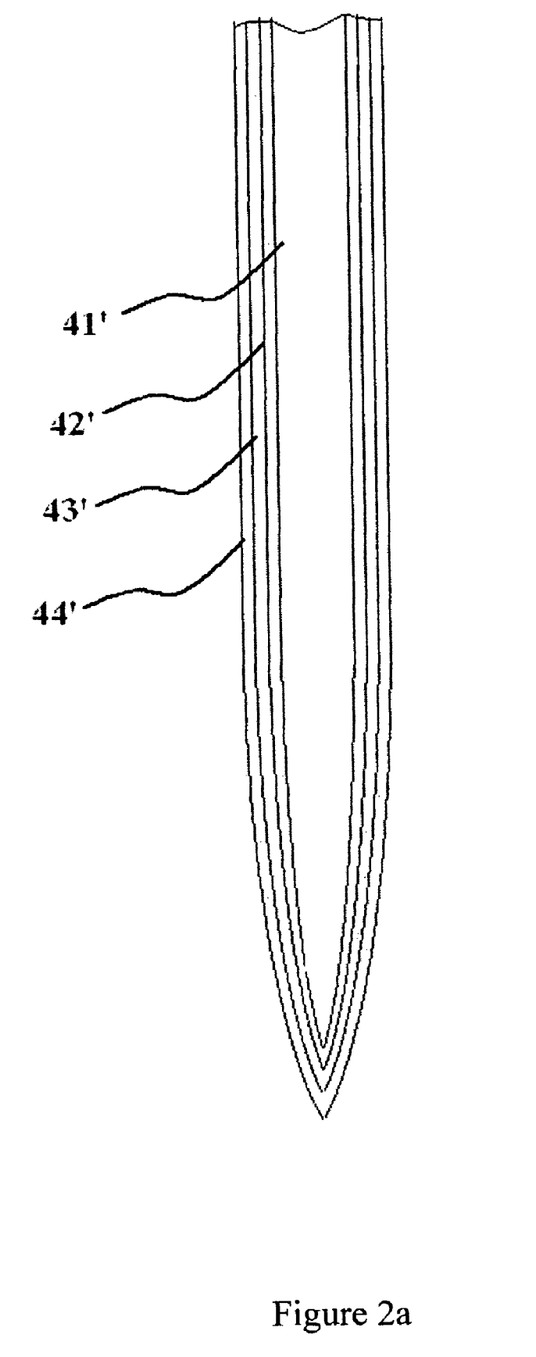
FIG. 2a is a cross section view of a needle cathode structure in accordance with the invention.

As seen in FIG. 2a, the cathode comprises a cathode needle core 41', a first cathode cover layer 42', a second cathode cover layer 43', and a third cathode cover layer 44', wherein the cathode needle core 41' is a needle shaped metal core in the center of the electrode, covered by the first cover layer 42', which in turn is covered by the second cover layer 43', which in turn is covered by the third cover layer 44'. In a preferred embodiment, the needle core 41' is a hard metal needle core; the first cover layer 42' is a silver layer; the second cover layer 43' is a silver chloride layer; and the third cover layer 44' is a polymer diffusion layer. This configuration is for hydrogen peroxide detection.

The biosensing layer is a complex membrane that comprises enzyme in the inner portion and biocompatible polymers in the outer portion. The surface layer of the membrane possesses molecular diffusion limiting characteristics.

In another embodiment of the invention, for an anode, the anode needle core 41 is a metal needle core; the first anode cover layer 42 is a silver layer; the second anode cover layer 43 is a polymer layer; and the third anode cover layer 43 is omitted. For a cathode, the cathode needle core 41' is a metal needle core; the first cathode cover layer 42' is a platinum layer; the second cathode cover layer 43' is a bio-sensing layer; and the third cathode cover layer 44' is omitted. This configuration is for oxygen detection.

The diameter of the needle electrode core in this invention may be in the range of 0.1-0.3 mm.

Figure 1A:
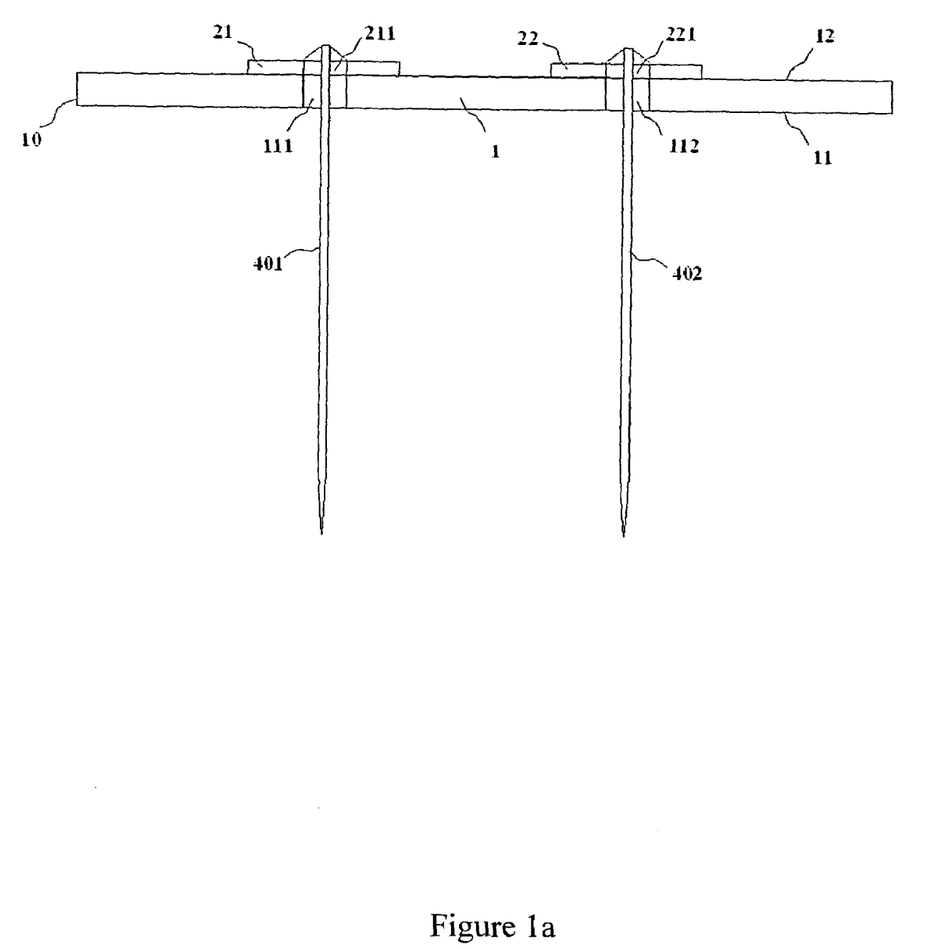
FIG. 1a is a cross section view of a two-electrode sensor assembly in accordance with a preferred embodiment of the invention.

As seen in FIG. 1a, in a preferred embodiment, a percutaneously implanted biosensor assembly 10 of the present invention comprises a base 1 with a planar bottom surface 11 and a top surface 12 sustaining a first connection plate 21 and a second connection plate 22, an anode 401 and an cathode 402 in elongated thin needle shapes fixed perpendicularly to the bottom surface 11 of the base 1 respectively. The base 1 of the sensor assembly 10 further comprises a first base mounting hole 111 and a second base mounting hole 112, wherein the first connection plate 21 and the second connection plate 22 further comprise a first plate mounting hole 211 and a second plate mounting hole 221 respectively, wherein the first plate mounting hole 211, second plate mounting hole 221 and the first base mounting hole 111, second base mounting hole 112 are in line with each other respectively, wherein the upper ends of the anode 401 and the cathode 402 penetrate the first base mounting hole 111, the second base mounting hole 112 and the first plate mounting hole 211, the second plate mounting hole 221, wherein the top ends of the anode 401 and the cathode 402 are affixed to the first connection plate 21 and second connection plate 22 respectively.

The base 1 is of non-conductive materials, serving as the physical support to the body of the biosensor assembly 10. The first base mounting holes 111 and the second base mounting hole 112 may be filled with non-conductive Epoxy to fix electrodes 401 and 402 to the base 1. The first plate mounting holes 211 and the second plate mounting hole 221 may be filled with conductive Epoxy, or may be soldered or welded with conductive materials for electric connection.

There may be a medical adhesive tape affixed to the bottom of the base for attaching the sensor assembly to the skin.

On the upper side of the base, there may be electric receptacles for connecting the electrodes to a signal reading instrument for processing, recording and reading the signals. The electrodes can also be connected through contact circuits with the signal reading instrument.

Figure 1B:
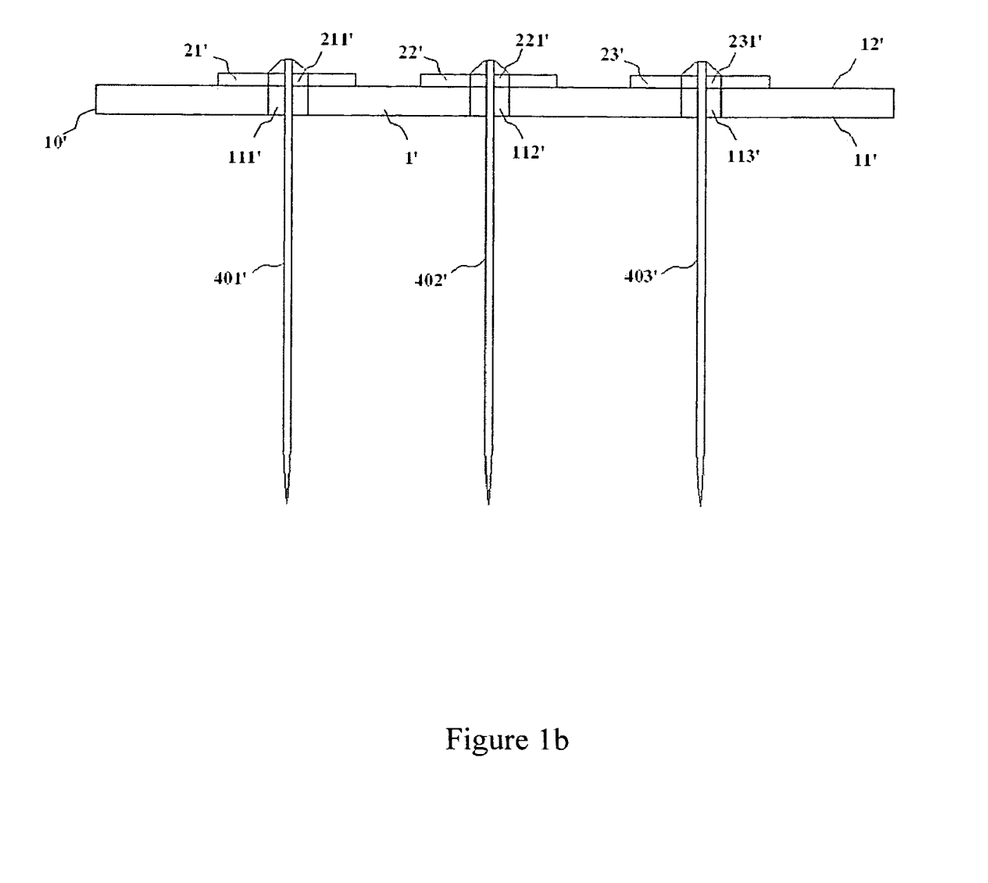
FIG. 1b is a cross section view of a three-electrode sensor assembly in accordance with a preferred embodiment of the invention.

As seen in FIG. 1b, in another preferred embodiment, a percutaneously implanted biosensor assembly 10' of the present invention comprises a base 1' with a planar bottom surface 11' and a top surface 12' sustaining a first connection plate 21', a second connection plate 22', and a third connection plate 23', an anode 401', and cathode 402', 403' in elongated thin needle shapes fixed perpendicularly to the bottom surface 11' of the base 1' respectively. The base 1' of the sensor assembly 10' further comprises a first base mounting hole 111', a second base mounting hole 112', and a third base mounting hole 113', wherein the first connection plate 21', the second connection plate 22' and the third connection plate 23' further comprise the first plate mounting hole 211', the second plate mounting hole 221', the third plate mounting hole 231' respectively, wherein the first plate mounting hole 211', the second plate mounting hole 221', the third plate mounting hole 231' and the first base mounting hole 111', the second base mounting hole 112', the third base mounting hole 113' are in line with each other respectively, wherein the upper ends of the anode 401', and the cathode 402', 403' penetrate the first base mounting hole 111', the second base mounting hole 112', the third base mounting hole 113' and the first plate mounting hole 211', the second plate mounting hole 221', the third plate mounting hole 231', wherein the top ends of the anode 401', and the cathode 402', 403' are affixed to the first connection plate 21', the second connection plate 22', and the third connection plate 23' respectively by electric conductive material.

The sensor assembly as shown in FIGS. 1a and 1b can be used for measuring glucose concentration in tissue fluid by measuring hydrogen peroxide produced from glucose oxidase catalyzed oxidizing reaction. For example, for a two electrode system, the anode has a diameter of approximately 0.2 mm, and is made of stainless steel, beryllium bronze, titanium alloy, or other hard alloy conductive material as core, electro plated by gold or platinum as inert electrode, plated by platinum. A compound sensing membrane is deposited to the electrode surface. The inner layer of the membrane contains glucose oxidase and the outer layer is of highly biocompatible polymer diffusion membrane. The glucose molecules in the tissue fluid diffuse through the outer portion of the membrane to reach the inner enzyme region, catalytically oxidized by oxygen and produce hydrogen peroxide. This process consumes equivalent amount of oxygen. The hydrogen peroxide produced can be oxidized on the anode by a higher than 0.5V (VS Ag/AgCl) voltage to form a current in the electric circuit of the measuring system. When the diffusion process of the glucose through the diffusion control membrane is the controlling process of the entire reaction process, the electric current through the sensing electrode is proportional to the glucose concentration of the surrounding tissue fluid. The electric current thus reflects the corresponding glucose concentration in the tissue fluid.

The cathode is made of stainless steel, beryllium bronze, titanium alloy, or other hard alloy conductive material as the core, plated by silver layer. It can also be made of hard silver-rich alloy as the core. The silver electrode surface is prepared with sufficient amount of silver chloride by electrochemical oxidation in potassium chloride solution or chemical chlorinating in ferric chloride solution. The outer surface of the cathode is a highly biocompatible polymer diffusion membrane.

The surfaces of the anode and cathode comprise platinum and silver chloride respectively, which form rough surfaces naturally by the preparing process. They will provide relatively higher surface area and sufficient roughness after chemical affixation. These surface characteristics make the attachment and affixation of the biosensing compound membrane readily achievable.

The biosensing layer is of a compound membrane. The inner portion contains glucose oxidase affixed by chemical cross-linking and the outer portion is a biocompatible polymer layer that could be used for measuring glucose concentration in the subcutaneous tissue fluid. The thickness of the compound membrane is not more than 10 micron.

Figure 1C:
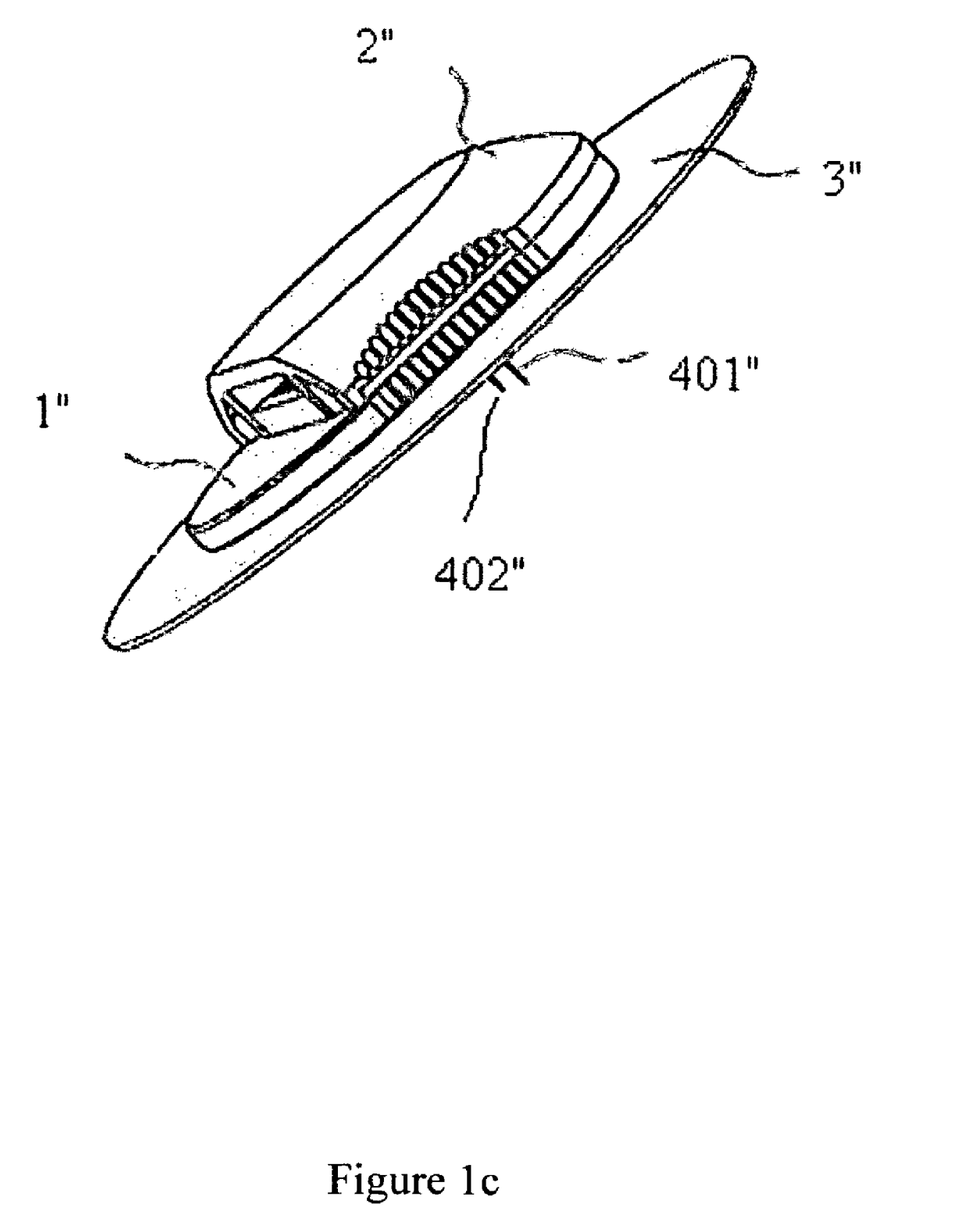
FIG. 1c is a perspective view of another two-electrode sensor assembly in accordance with a preferred embodiment of the invention (partially exposed)

In another preferred embodiment, as shown in FIG. c, a percutaneously implanted biosensor assembly 10" comprises a molded insulating plastic base 1", a needle anode 401", a needle cathode 402", a mold plastic cover 2", and a circular medical adhesive tape 3". The needle anode 401" and needle cathode 402" are parallel to each other, and perpendicular to the bottom of the base 1". Conducting circuits are on the top of the base 1" and covered by mold plastic cover 2" for electric connection between anode 401", cathode 402" and an external portable amperometric device. The circular medical adhesive tape 3" are fixed to the planar bottom of the base 1". A pair of electric receptacles for connecting the electrodes with the amperometric device are located on the molded insulating plastic base 1" and connected to conducting circuits. The anode 401" has a stainless steel needle core (diameter: 0.16 mm), covered by a gold layer, a platinum layer, and biosensing membrane layer. The needle cathode 402" has a stainless steel needle core, covered by a silver layer, a silver chloride layer and a polymer protective layer. The biosensing membrane is a complex membrane. Its inner layer contains enzyme oxidase and the outer layer is of polymeric diffusion membrane, with a thickness of approximately 2-8 micrometer. The diffusion membrane is structured with blend of polydimethysiloxane-polyurethane copolymer, hydrophilic polymers and ionic conducting materials.

Figure 3:
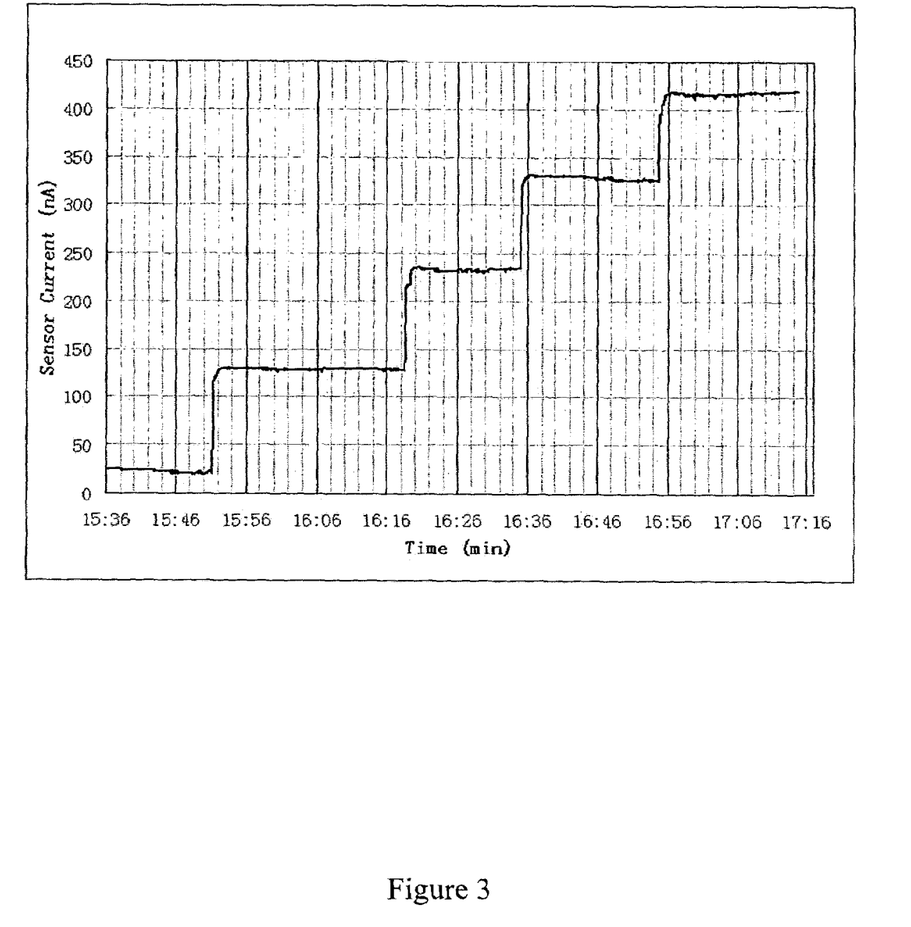
FIG. 3 is a graph showing the sensor response in phosphate buffer to incremental glucose increase.

The sensor has a typical response time of less than 30 seconds to an instantaneous glucose concentration change. Linear response range of the glucose concentration is not less than 20 mmole/L. FIG. 3 illustrates the response current signal of a sensor assembly in phosphate buffer during a step incremental increase of glucose. In the graph, each increase in current represents the response to the addition of 5 mmol/L glucose. Y-axis is the response current in nA.

Figure 4:
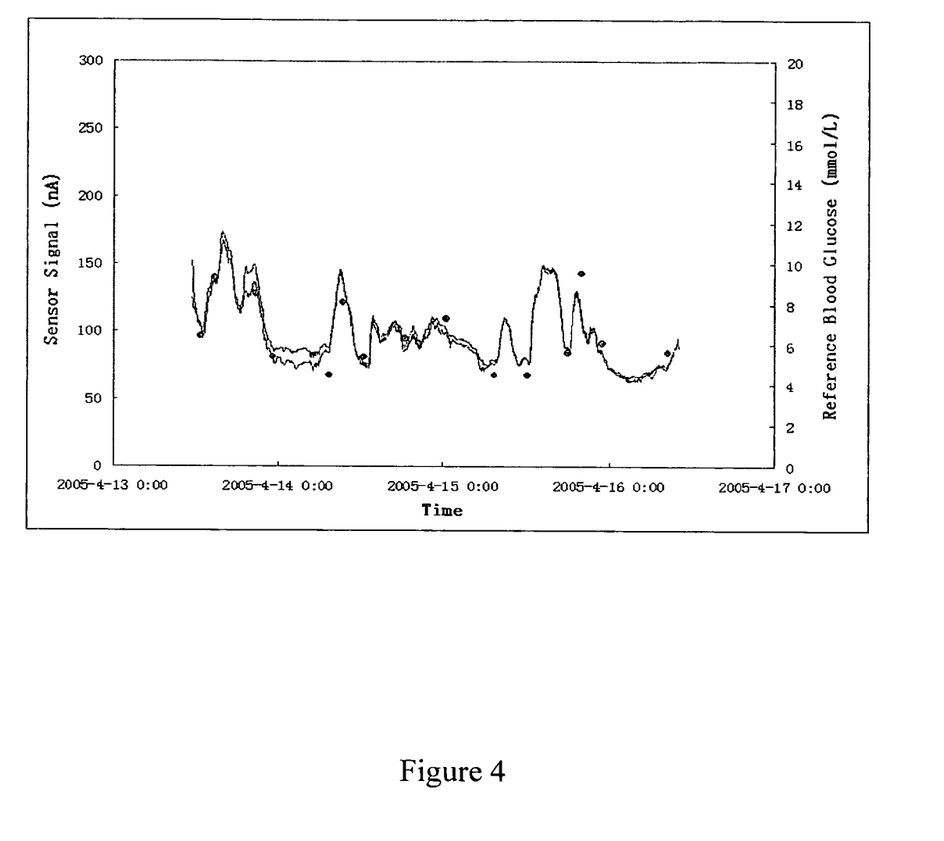
FIG. 4 is a graph showing the signals of two independent sensor assemblies implanted in the upper arm of a type 2 diabetes patient during a 72 hour period. (Dots are finger capillary reference glucose values measured by the patient with a commercial glucose meter. The sensor signals demonstrate good agreement with each other and close correlation with the reference blood glucose. There is no signal drift during the entire period of monitoring.)

The sensor of this invention, when used in clinical test, demonstrates superior performance as illustrated in FIG. 4. For a 3-day period of in vivo test, two sensor assemblies are implanted in the upper arm of a type 2 diabetes patient. These two sensor assemblies produced nearly identical signals for the entire duration. The continuous lines in FIG. 4 represent the raw sensor signals. Circular dots are values from finger tip capillary blood glucose measurements (in mmol/L) using a conventional blood glucose meter. The graph shows that the sensor possess high sensitivity, reproducibility and stability.

The needle sensor system in the present invention may be also configured with one anode and two or more cathodes connected in series or parallel to form multi-electrochemical systems; or, the system can be configured to have one cathode and two or more anodes to form multi-electrochemical systems.

The anode in the present invention features layers of noble metal, platinum and biosensing layers over a rigid non-corrosive conducting needle. The cathode, on the other hand, comprises layers of silver, silver chloride and polymer over a rigid non-corrosive conducting needle. The cathode body may also be formed using a silver alloy needle and covering the surface with silver chloride.

The biosensing layer is of a compound membrane. The inner portion contains enzyme and the outer portion is of biocompatible polymers that features minimal tissue reactions. The enzyme provides biospecificity, to selectively react with the desired chemical species to convert it into electrochemically active molecules. Typical enzymes may be glucose oxidase, alcohol oxidase, lactate oxidase, and cholesterol oxidase, etc., The membrane may be deposited and immobilized onto the electrode surface through chemical bonding by cross-linking reagents that have two reactive groups. The outer diffusion layer may be of medical grade polydimethylsiloxane copolymer or polymer blend.

The sensor membrane can be formed from a mixed solution of two different polymers. One of the polymers is hydrophilic and the other hydrophobic. A process of solvent evaporation from such a solution is used to prepare the membrane. Usually, the resulting membrane tends to form a non-homogeneous structure. The surface layer is typically hydrophobic which is not permeable to most of water soluble molecules except oxygen.

To achieve the desired molecular permeability for measuring soluble molecules in aqueous environment, next step involves membrane re-structuring. It requires a special solvent mixture containing a cross-linking reagent to partially dissolve the membrane surface and then re-form the outermost layer in such a way that its composition is re-arranged to be permeable to desired molecules. The cross-linking reagent serves to fix the new structure as it forms.

The hydrophilic polymer can be one or more of a number of commercial hydrophilic polymers such as polyethylene glycol and its derivatives with end reactive groups. The hydrophobic polymer can be one or more of a class of copolymers that contain polydimethylsiloxane (silicone) as one of the components for a favorable oxygen permeability. Examples are medical grade silicone-polyurethane copolymers, silicone-polycarbonate copolymers, and silicone-methacrylate copolymers.

In a preferred embodiment, said hydrophilic polymer is amine terminated polyethylene glycol, the hydrophobic polymer is polydimethysiloxane-polyurethane copolymer, and the cross-linking reagent is glutaraldehyde. The dry weight ratio of the hydrophilic polymer vs hydrophobic polymer may be in the range of 1:19 to 1:3, adjustable on the bases of the membrane ionic conductivity as well as glucose molecular permeability. The polymers may be prepared and used in 3%-7% (weight/volume) solutions in a solvent in which all polymers have sufficient solubility. The special mixture solvent for membrane surface modification may contain water, tetrahydrofuran(THF), and ethanol in volume concentrations of 25%±15%, 65%±25%, and 10%±10%, respectively. The percentage of the three constituents may be adjusted in the given ranges based on the need of the overall sensitivity requirement.

To reproducibly deposit various solutions onto the electrode surface to form a homogeneous membrane, the following three methods may be used. 1) Dip-coating:

Submerge the electrode into a solution and remove it in a preferred angle, spin rate and linear speed to coat a uniform film on the electrode; 2) Spray coating: Spin the electrode horizontally in a nebulized stream of the solution under a controlled spray nozzle to form the film; And 3) Loop-coating: Load a wire loop of adequate diameter with the solution such that a liquid film is formed inside the loop (similar to a bubble blower), and then move the electrode perpendicularly to penetrate the middle of the loop to transfer a liquid film onto the electrode.

The thickness of the biosensing membrane may be in the range of 2-10 micron, in which the enzyme layer may have the thickness of 1 micron and the diffusion layer may have a thickness of less than 9 micron.

For using the sensor in the present invention, the needles are directly inserted into the skin. The adhesive tape affixes the sensor base to the skin. Analyte molecules (e.g. glucose) in the surrounding tissue fluid diffuse through the outer membrane to reach the enzyme layer, catalytically oxidized by oxygen, producing hydrogen peroxide. The latter in turn is electrochemically oxidized on the platinum electrode (polarized at 0.5-0.6V vs Ag/AgCl) to form a current in the electrode circuit. The magnitude of the current is proportional to the concentration of glucose. The current is converted into concentration information and recorded by an external electronic device for display and analysis.

What is claimed is:

1. A percutaneously implanted miniature sensor assembly, comprising a base, an anode, a reference cathode, an assisting cathode, a first contact plate, a second contact plate and a third contact plate; wherein the base further comprises a first mounting hole surface, a second mounting hole surface, a third mounting hole surface, a base top surface and a base bottom surface, wherein the first mounting hole surface defines a first mounting hole, the second mounting hole surface defines a second mounting hole, and the third mounting hole surface defines a third mounting hole; wherein the first contact plate further comprises a first plate mounting surface defining a first plate mounting hole, the second contact plate further comprises a second plate mounting surface defining a second plate mounting hole, and the third contact plate further comprises a third plate mounting surface defining a third plate mounting hole respectively; wherein the first contact plate, the second contact plate and the third contact plate are set on the base on the base top surface, wherein the first plate mounting hole, the second plate mounting hole, the third plate mounting hole are in line with the first mounting hole, the second mounting hole and the third mounting hole respectively; wherein the anode, the referencing cathode and the assisting cathode are in needle shape and implantable in a body, wherein the upper end of the anode penetrated the first plate mounting hole and the first mounting hole, the upper end of the referencing cathode penetrated the second plate mounting hole and the second mounting hole, and the upper end of the assisting cathode penetrate the third plate mounting hole and the third mounting hole, wherein the top of the anode, the referencing cathode and the assisting cathode are connected with the first contact plate, the second contact plate, and the third contact plate by electric conductive material, wherein the anode, the referencing cathode and the assisting cathode are perpendicular to the base bottom surface respectively.

* * * * *